United States Patent [19]

LaMarche, Jr. et al.

[11] Patent Number: 4,569,069

[45] Date of Patent: Feb. 4, 1986

[54] DRAINAGE PROFILE TESTER FOR PAPERMAKING

[75] Inventors: Louis J. LaMarche, Jr.; G. Roy Jones, both of Raleigh, N.C.

[73] Assignee: Huyck Corporation, Wake Forest, N.C.

[21] Appl. No.: 546,512

[22] Filed: Oct. 28, 1983

[51] Int. Cl.[4] .............................................. G01B 15/02
[52] U.S. Cl. .................................... 378/89; 250/308; 250/390 D
[58] Field of Search ............... 378/89, 90; 250/390 C, 250/390 D, 390 E, 308

[56] References Cited

U.S. PATENT DOCUMENTS

| | | | |
|---|---|---|---|
| 3,426,200 | 2/1969 | Lehman | 378/89 |
| 3,668,397 | 6/1972 | Stucky | 378/89 |

*Primary Examiner*—Craig E. Church
*Attorney, Agent, or Firm*—Pahl, Lorusso & Loud

[57] ABSTRACT

An apparatus and method for measuring the amount of papermaking stock on a moving fabric in a fourdrinier papermaking machine, including a backscattering mass sensing device and a hydrofoil blade adapted to scrape water from the underside of the fabric and to support the mass sensing device in close proximity to the papermaking belt.

7 Claims, 3 Drawing Figures

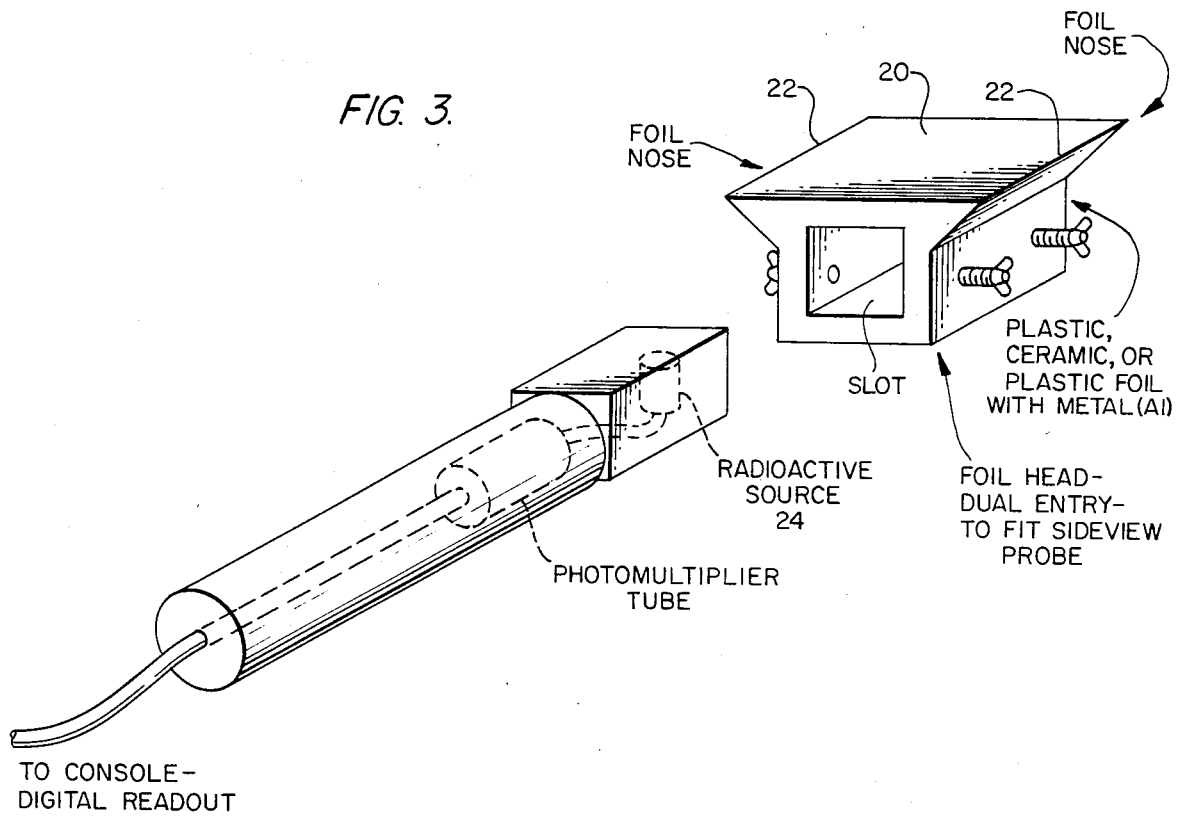

DRAINAGE PROFILE TESTER FOR PAPERMAKING

BACKGROUND OF THE INVENTION

This application relates to a device for measuring the amount of papermaking stock on a moving fabric or wire during operation of a fourdrinier paper machine.

During the operation of a papermaking machine, it is important to continuously measure the consistency of the pulp and water mixture of the fourdrinier tables. This allows the papermaker to make adjustments to the drainage table. It is important to make these adjustments because in order to obtain a quality paper product the water must drain from the pulp at a certain rate in various sections of the fourdrinier table.

Prior art devices for measuring consistency on a fourdrinier table have serious drawbacks. One such device is an ultrasonic sensing device. This device requires a special supporting beam so it can be placed under the fourdrinier table. However, this beam is so bulky as not to allow measurements to be taken between closely spaced drainage units.

Consistency measurements have also conventionally been made by obtaining blow samples. This involves the stock being blown into a container by compressed air underneath it. The stock can then be measured for consistency. However, this method produces holes in the stock. The paper produced in the area of where the measurements were taken must then be scrapped. Normally, the total machine productivity must be curtailed to allow the series of blow tests. This waste of paper is obviously not economical.

SUMMARY OF THE INVENTION

An object of this invention, therefore, is to provide an apparatus that will accurately measure the consistency of the pulp and water mixture on the fourdrinier table.

Other objects and advantages will become apparent hereinafter.

According to the present invention, the above-stated objective as achieved by using a backscattering device mounted in close proximity to the underside of the fabric surface. The apparatus of the present invention includes a special foil blade adapted to hold the backscattering device in place and to provide a smooth surface flat against the underside of the fabric (the surface opposite that supporting the paper stock) so as to remove water clinging to the underside surface.

IN THE DRAWINGS

FIG. 3 is an isometric representation of another embodiment of a foil blade/backscattering device in accordance with the present invention.

DESCRIPTION OF THE PREFERRED EMBODIMENT

The foil blades conventionally used in the forming section of a papermaking machine are keyed to slide onto a mounting block. Both the mounting block and foil extend across the width of the fabric. Each foil blade (commonly used in groups) is mounted to present a leading edge in contact with the underside of the travelling fabric and a top surface trailing away from the leading edge at an angle of 2° to 5° with respect to the fabric. In this manner a vacuum is formed between the fabric and the top surface of the foil blade, which vacuum serves to draw water out of the paper stock supported on the fabric. The water so drawn out tends to cling to the underside of the fabric.

The foil blade of the present invention is similar but has a smooth, upper fabric-contacting surface that is oriented, with respect to the key, keyway or other mounting means on its lower surface, to contact the underside of the travelling fabric flat (at a 0° angle). Accordingly, the blade of the present invention clears the underside of the fabric of any clinging water and presents such a water-free surface to the backscattering device mounted therein.

Figure 1:
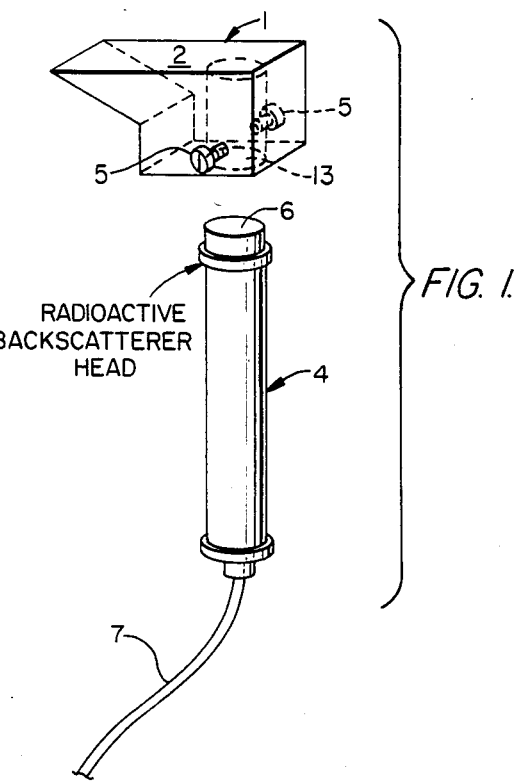
FIG. 1 is an isometric representation of the foil blade holding the head of a backscattering device in accordance with the present invention.

As depicted in FIG. 1, the foil blade, generally designated by the numeral, 1 may be fabricated of ceramic, high-density polyethylene or a similar high-temperature plastic material. High density polyethylene is presently preferred. The upper surface 2 of the foil blade is smooth to allow contact flush with the underside of the forming fabric or wire where it will effect removal of excess water clinging to the underside of the fabric. Removal of water clinging to the underside of the fabric eliminates an amount of mass (water) which would otherwise be a variable in the determination and allows for a reading truly representative of the consistency of the paper stock-supported on the fabric surface. The foil blade 1 of this preferred embodiment is provided with a hole 3 which is bored from the bottom surface of the foil blade to accommodate a backscattering device 4. Set screws 5 or some other positioning means are used to hold the head 6 of the backscattering device 4 flush against the end of the bore 3 which is ⅛ inch from the upper surface of the foil blade 1. The head of the mass sensing device 4 is connected by a cable 7 to an instrument panel (not shown) where the total mass of the pulp and water mixture can be recorded or read directly on a digital readout.

FIG. 3 depicts one embodiment similar to that of FIG. 1 but considered an improvement thereover for its compactness and reversibility. Thus, foil 20 is provided with a pair of noses 22. The dual-nose foil head 20 allows the foil to be reversibly mounted, i.e., it can be mounted with the leads extending to either side of the machine. The side entry for the radioactive probe allows the unit to fit between closely spaced belt runs on a Fourdrinier machine.

Any type of backscattering device, electron, neutron or gamma, may be utilized. However, a gamma guage is preferred for ease and safety of operation. In our experimental work, we have employed a model RPD104 gamma guage manufactured by NDC Systems of Duarte, Calif.

EXAMPLE

Figure 2:
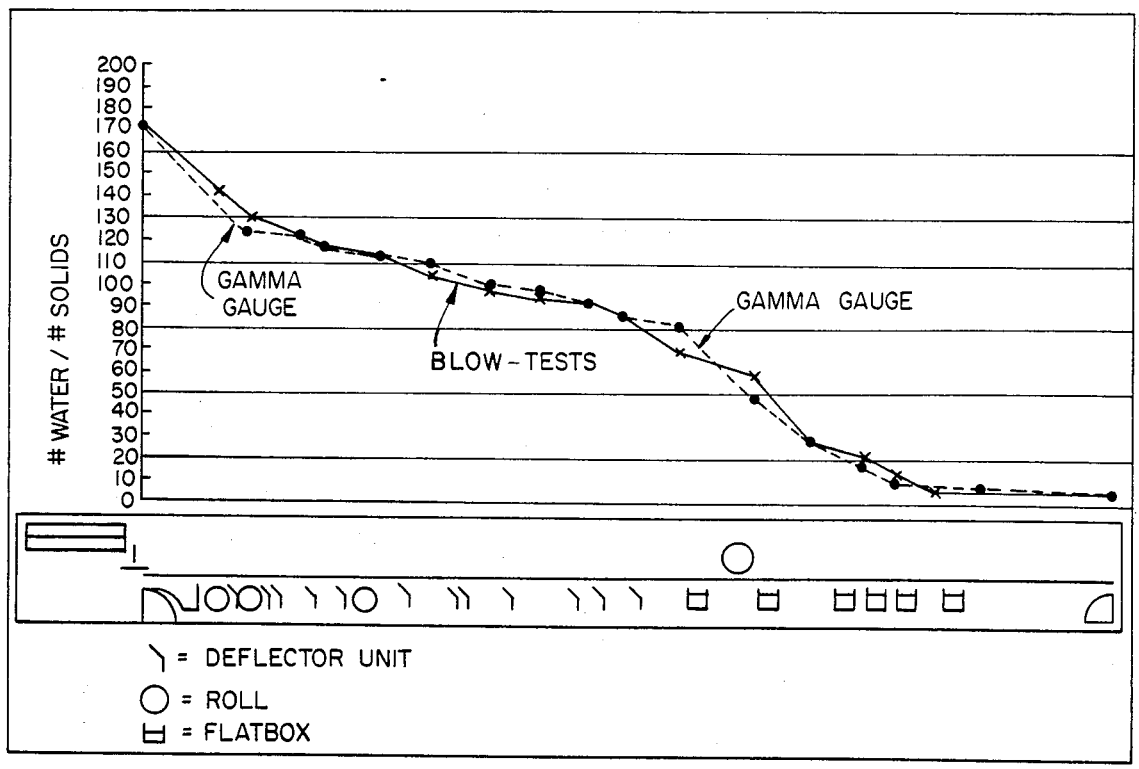
FIG. 2 is a graph showing data of a moisture profile generated in accordance with the present invention.

The drainage profile down the table of a papermaking machine producing 51# bleached backing paper at 1414 fpm was determined with a high density polyethylene foil blade as depicted in FIG. 1 and containing a type 104RPD gamma gauge manufactured by NDC Systems, Durate, Calif. The foil blade was inserted between the second table roll and the second deflector unit, and the total mass was measured in # mass/1000 sq. ft. Subsequent measurements were made after the fourth deflector unit, after the fifth deflector unit, after the third table roll, after the sixth deflector unit, after the eigthth deflector unit, after the ninth deflector unit, after the tenth deflector unit, after the eleventh deflector unit, before the first flatbox, after the first flatbox, after the second flatbox, between the third and fourth flatboxes, between the fourth and fifth flatboxes, after the fifth flatbox and before the couch. All of these values were taken in # mass/1000 sq. ft. and converted to # water/# solids by the standard mass balance formulae. A drainage profile was then developed. At the same time, the opportunity for blow tests presented itself, and these were taken and compared against the gamma gauge readings. Both sets of data are shown in the graph of FIG. 2. The result in correlation between these two drainage profiles is 0.952 sigma value.

From these measurements, taken at different locations, a drainage profile can be determined by a simple mass balance to indicate the drainage, or water removed, from the stock by drainage elements such as foil blades, table rolls, suction boxes, etc.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed:

1. A method for measuring the consistency of a paper stock mixture of paper pulp and water carried by a travelling papermaker's forming belt over a stationary point, said method comprising:

placing a backscattering device at said stationary point;

removing water clinging to the underside surface of the belt to present a belt surface free of clinging water above said stationary point by pressing a flat edge member against the underside of said travelling belt, said flat edge member serving to support said backscattering device at said stationary point; and converting the value of the output of said backscattering device to a value for the mass or consistency of the paper stock.

2. The process of claim 1 wherein said flat edge member contacts said belt at a 0° angle.

3. The process of claim 1 wherein said backscattering device is a gamma gauge.

4. Apparatus for measuring the consistency of a paper stock mixture of paper pulp and water on a travelling papermaker's forming belt, at a stationary point over which the belt passes, said apparatus comprising:

a backscattering device for measuring the mass of the paper stock on the belt where the belt passes over said stationary point; and means for supporting said backscattering device under a run of said belt, said supporting means having a smooth flat edge portion for engaging the travelling belt across at least a portion of the width of the belt to remove water clinging from the lower surface of said belt portion.

5. The apparatus of claim 4 wherein said backscattering means is a gamma gauge.

6. The apparatus of claim 4 wherein said support means is a foil blade.

7. The apparatus of claim 6 wherein said foil blade has a smooth surface, for contacting the belt, oriented with respect to said mounting means to contact the belt at a 0° angle.

* * * * *